United States Patent
Benning et al.

(10) Patent No.: US 12,053,921 B2
(45) Date of Patent: Aug. 6, 2024

(54) PRINTING APPARATUS AND METHOD

(71) Applicant: University of Newcastle upon Tyne, Tyne and Wear (GB)

(72) Inventors: Matthew James Benning, Tyne and Wear (GB); Kenneth William Dalgarno, Tyne and Wear (GB)

(73) Assignee: University of Newcastle upon Tyne, Tyne and Wear (GB)

(*) Notice: Subject to any disclaimer, the term of this patent is extended or adjusted under 35 U.S.C. 154(b) by 0 days.

(21) Appl. No.: 18/365,542

(22) Filed: Aug. 4, 2023

(65) Prior Publication Data
US 2024/0017477 A1 Jan. 18, 2024

Related U.S. Application Data

(63) Continuation of application No. 16/627,545, filed as application No. PCT/GB2018/051908 on Jul. 5, 2018, now Pat. No. 11,945,153.

(30) Foreign Application Priority Data

Jul. 5, 2017 (GB) .................... 1710834.1

(51) Int. Cl.
*B29C 64/112* (2017.01)
*B29C 64/209* (2017.01)
(Continued)

(52) U.S. Cl.
CPC .......... *B29C 64/112* (2017.08); *B29C 64/209* (2017.08); *B29K 2105/0061* (2013.01);
(Continued)

(58) Field of Classification Search
CPC ...... B29C 64/112; B29C 64/209; B33Y 30/00
See application file for complete search history.

(56) References Cited

U.S. PATENT DOCUMENTS

| | | |
|---|---|---|
| 2011/0280914 A1 | 11/2011 | Prestwich et al. |
| 2018/0029361 A1 | 2/2018 | Jeuté |
| 2018/0370117 A1 | 12/2018 | Gardiner et al. |

FOREIGN PATENT DOCUMENTS

| | | |
|---|---|---|
| DE | 3501905 A1 | 12/1985 |
| DE | 102006048460 A1 | 4/2008 |

(Continued)

OTHER PUBLICATIONS

International Search Report and Written Opinion issued in corresponding application No. PCT/GB2018/051908, dated Sep. 24, 2018, 14 pages.
(Continued)

*Primary Examiner* — James Sanders
(74) *Attorney, Agent, or Firm* — Meunier Carlin & Curfman LLC

(57) ABSTRACT

A printing apparatus and method. The printing apparatus is for impinging liquids from at least two liquid sources. The apparatus comprises a first jet actuator configured to dispense a first liquid from a first liquid source and a second jet actuator configured to dispense a second liquid from a second liquid source. The apparatus further comprises an adjustment element configured to adjust a trajectory of at least the first liquid dispensed from the first jet actuator such that the first liquid impinges the second liquid dispensed from the second jet actuator.

19 Claims, 17 Drawing Sheets

(51) Int. Cl.
*B29K 105/00* (2006.01)
*B33Y 10/00* (2015.01)
*B33Y 30/00* (2015.01)
*B33Y 70/10* (2020.01)

(52) U.S. Cl.
CPC .............. *B33Y 10/00* (2014.12); *B33Y 30/00* (2014.12); *B33Y 70/10* (2020.01)

(56) References Cited

FOREIGN PATENT DOCUMENTS

| | | |
|---|---|---|
| EP | 3069884 A1 | 9/2016 |
| GB | 2539165 A1 | 12/2016 |
| JP | 11227192 | 8/1999 |
| JP | 11227227 | 8/1999 |
| WO | 2014197999 A1 | 12/2014 |
| WO | 2016091336 A1 | 6/2016 |
| WO | 2016135294 A2 | 9/2016 |

OTHER PUBLICATIONS

Search Report under Section 17(5) issued in corresponding application No. GB1710834.1, dated Jan. 4, 2018, 2 pages.
Murphy, Sean V., and Anthony Atala. "3D bioprinting of tissues and organs." Nature biotechnology 32.8 (2014): 773-785.

PRINTING APPARATUS AND METHOD

CROSS REFERENCE TO RELATED APPLICATIONS

This application is a continuation of, and claims the benefit of, U.S. patent application Ser. No. 16/627,545, filed Dec. 30, 2019, which is a national stage application filed under U.S.C. § 371 OF PCT International Application No. PCT/GB2018/051908, filed Jul. 5, 2018, which claims the benefit of GB Application No. 1710834.1 filed on Jul. 5, 2017, the contents of which are each hereby incorporated by reference in their entirety.

FIELD OF THE DISCLOSURE

The present invention relates to a printing apparatus and method. In some aspects, the present invention relates to a printing apparatus and method for impinging liquids from first and second liquid sources. The apparatus and method may be particularly suited to bioprinting.

BACKGROUND

Recent advances in additive manufacturing (three-dimensional printing) have led to the printing of biocompatible materials. Such 3D bioprinting can be used to create complex 3D co-cultures, which may subsequently be used as tissues and organs suitable for transplantation, for example.

However, current 3D bioprinting technologies are limited by the printing liquids having a relatively high viscosity, which can make them difficult to process. The printing apparatus can become blocked by high viscosity liquids and pressure in the apparatus and shear stresses can damage cells in the liquid.

Murphy & Atala, 3D bioprinting of tissues and organs, Nature Biotechnology 32(8), 773-785 (2014) describe various 3D bioprinting approaches including inkjet bioprinters, microextrusion bioprinters, and laser-assisted bioprinters. However, each of these approaches can be limited by material rheology, resolution, speed of printing and compatibility with biologically relevant materials.

One approach that has been used is to mix gel pre-cursors in a mixing cartridge prior to deposition. The gel pre-cursors have a relatively lower viscosity and when mixed they react to form a relatively higher viscosity gel which can be deposited onto a substrate. However, this method still has a risk of the gel becoming blocked in the cartridge.

It would therefore be useful to provide an apparatus that is suitable for depositing high viscosity liquids in a 3D printing system with a higher throughput (printing speed), better reliability and higher resolution.

SUMMARY

According to a first aspect of the present invention there is provided a printing apparatus for impinging liquids from at least two liquid sources. In one embodiment, the apparatus comprises: a first jet actuator configured to dispense a first liquid from a first liquid source; a second jet actuator configured to dispense a second liquid from a second liquid source; and an adjustment element configured to adjust a trajectory of at least the first liquid dispensed from the first jet actuator such that the first liquid impinges the second liquid dispensed from the second jet actuator.

In some embodiments, the adjustment element is configured to adjust the position of the first jet actuator relative to the second jet actuator to adjust the trajectory of the first liquid dispensed from the first jet actuator.

In some embodiments, the adjustment element is configured to effect translational movement of the first jet actuator with respect to the second jet actuator.

In some embodiments, the adjustment element is configured to effect rotational movement of the first jet actuator.

In some embodiments, the adjustment element comprises an actuating element for adjusting the position of the first jet actuator.

In some embodiments, the adjustment element further comprises a controller to control the actuating element.

In some embodiments, the adjustment element further comprises a biasing element arranged to oppose the force of the actuating element on the first jet actuator.

In some embodiments, the adjustment element further comprises a further biasing element arranged to apply a force to the first jet actuator to control rotational movement of the first jet actuator upon actuation of the actuating element.

In some embodiments, the first jet actuator is mounted eccentrically in a collet, and wherein the actuating element is configured to rotate the collet to linearly adjust position of first jet actuator with respect to the second jet actuator.

In some embodiments, the adjustment element is configured to apply a force to the first liquid after it is dispensed from the first jet actuator to adjust the trajectory of the first liquid.

In some embodiments, the adjustment element comprises electrically charged deflection plates for applying an electrostatic force to the first liquid.

In some embodiments, the charged deflection plates are positioned adjacent to an exit nozzle of the first jet actuator.

In some embodiments, the first and second jet actuators are configured as drop-on-demand actuators.

In some embodiments, the apparatus further comprises a jet controller for controlling the release of the first and second liquids from the respective first and second jet actuators.

According to a another aspect of the present invention, there is provided a method of 3D printing. In one embodiment, the method comprises: providing a first jet actuator configured to dispense a first liquid from a first liquid source; providing a second jet actuator configured to dispense a second liquid from a second liquid source; adjusting a trajectory of at least the first liquid dispensed from the first jet actuator such that the first liquid impinges and combines with the second liquid dispensed from the second jet actuator; and depositing the combined first and second liquid on a substrate.

In some embodiments, the method of the second aspect is a method of 3D bioprinting.

In some embodiments, the first liquid comprises a first gel precursor and the second liquid comprises a second gel precursor.

In some embodiments, at least one of the first and second gel precursors comprise biological materials.

In some embodiments, the first liquid comprises a first reactive polymer precursor and the second liquid comprises a second reactive polymer precursor.

Some embodiments of the present invention provide a printing apparatus that is more suitable for printing of biological materials than previously known devices.

Some embodiments of the present invention allow for a more efficient printing process than previously known devices.

Some embodiments of the present invention allow for consistency in printing with increased repeatability.

Some embodiments of the present invention provide significantly higher productivity compared to previously known printing methods.

BRIEF DESCRIPTION OF THE DRAWINGS

Some embodiments of the present invention are further described hereinafter with reference to the accompanying drawings, in which:

FIG. 2 illustrates an example of a jet actuator used in printing apparatus of FIG. 1a;

In the drawings like reference numerals refer to like parts.

DETAILED DESCRIPTION

Figure 1A:
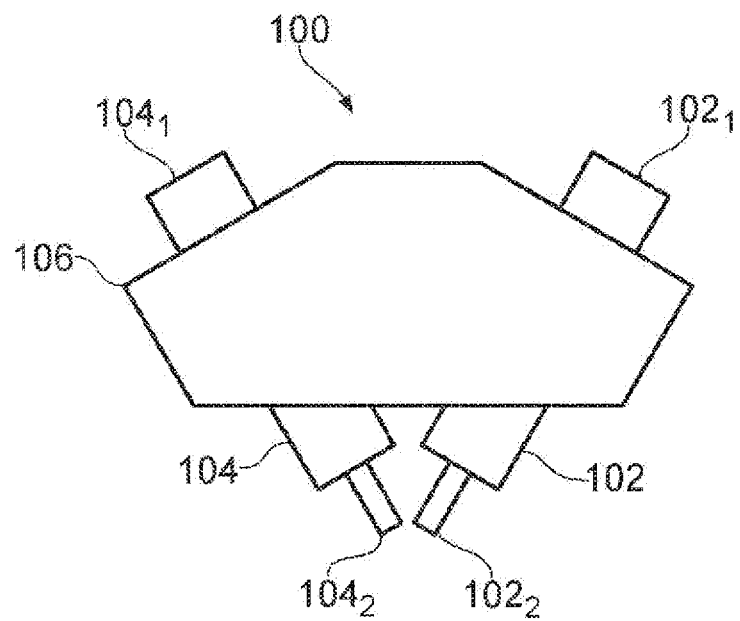
FIG. 1a illustrates a first example of a printing apparatus.
Figure 1B:
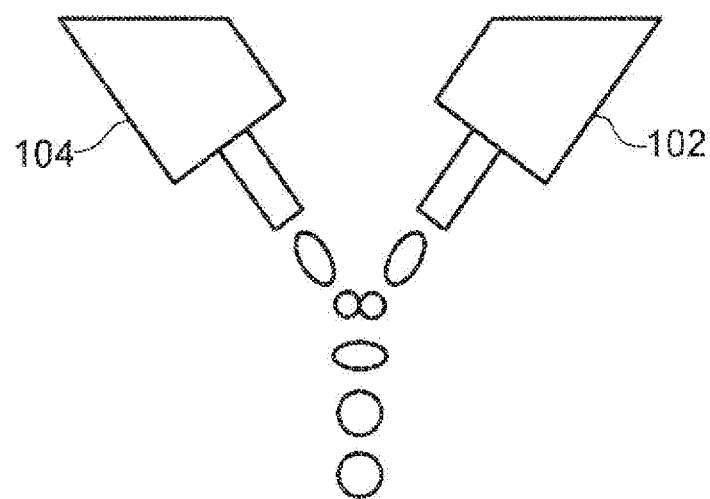
FIG. 1b illustrates the printing apparatus of FIG. 1a in use.
Figure 2:
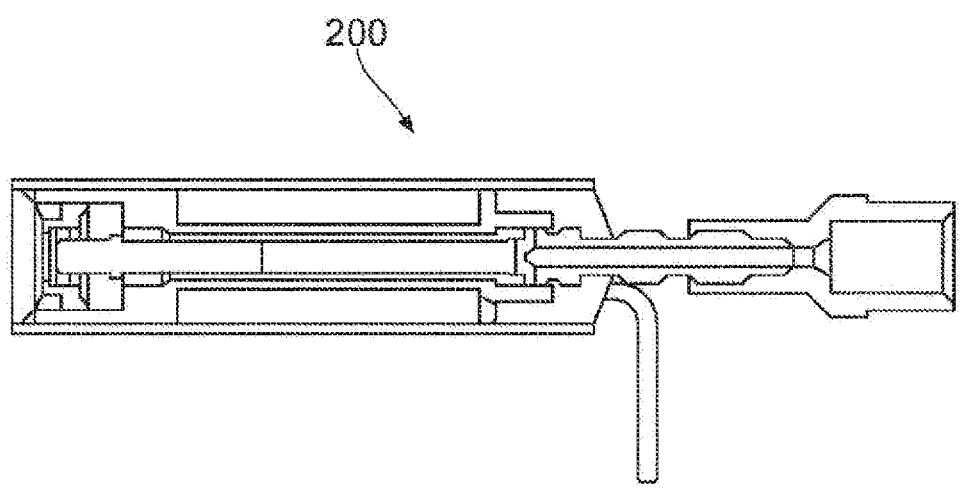

FIGS. 1a, 1b and 2 illustrate a first example of a printing apparatus 100 for impinging liquids from at least two liquid sources. The printing apparatus 100 includes a first jet actuator 102 configured to dispense a first liquid from a first liquid source; and a second jet actuator 104 configured to dispense a second liquid from a second liquid source such that the first liquid impinges the second liquid dispensed from the second jet actuator.

In this example, the first and second jet actuator 102, 104 are mounted within a jetting head 106. In use, first ends $102_1$ and $104_1$ of first and second jet actuators 102,104, receive first and second liquids from first and second liquid sources (not shown) respectively. In one example, the liquid source may be a hyperbaric container, or a container with a pressure head. The second ends $102_2$ and $104_2$ of first and second jet actuators 102,104 are configured to dispense said first and second liquids, respectively. For example, the second ends of each of the first and second jet actuators may include an exit orifice.

FIG. 1b illustrates printing apparatus 100 in use. The first and second liquids are dispensed from first and second jet actuators 102,104 at predetermined trajectories, such that the first and second liquids impinge. As such, the first and second liquid coalesce, or combine together to form a single droplet.

The printing apparatus 100 includes first and second jet actuators that form an operational pair of jet actuators. The printing apparatus 100 includes a single pair of jet actuators, however there may be any number of pairs of jet actuators mounted within a jetting head, for example there may be two, three or more pairs of individually addressable jet actuators.

FIG. 2 illustrates an example of a first jet actuator 200. In this example, the jet actuator is a microvalve jet actuator and is electromagnetically operated. In this example, the microvalve jet actuator may be a commercially available jet actuator from 'Lee Products Limited (UK)'. Other suitable jet actuators may also be used. For example, the jet actuator may be a microvalve or an inket or the like. The jet actuator may be operated by any suitable means. For example, the actuator may be operated by electromagnetics, thermal energy, piezo materials, pneumatics or hydraulics.

The jet actuator may be suitable for 'drop on demand' delivery of liquids. In other words, the jet actuator may be suitable for dispensing a single droplet of liquid at a time as and when required. It will be appreciated however, that a continuous inkjet method may also be applied.

In this example, the second jet actuator 104 is of the same type as the first jet actuator 102. In other examples the first and second jet actuators may be of different types.

The above described printing apparatus may be used in a jetting process for deposition onto a substrate. In some examples, the jetting process may be controlled by software. In such examples the software may compile images or code into a raster printing path. The printing path of the printing apparatus, i.e. the number of drops and their placement on the substrate may be produced considering the print velocity and droplet density per given area.

Figure 3A:
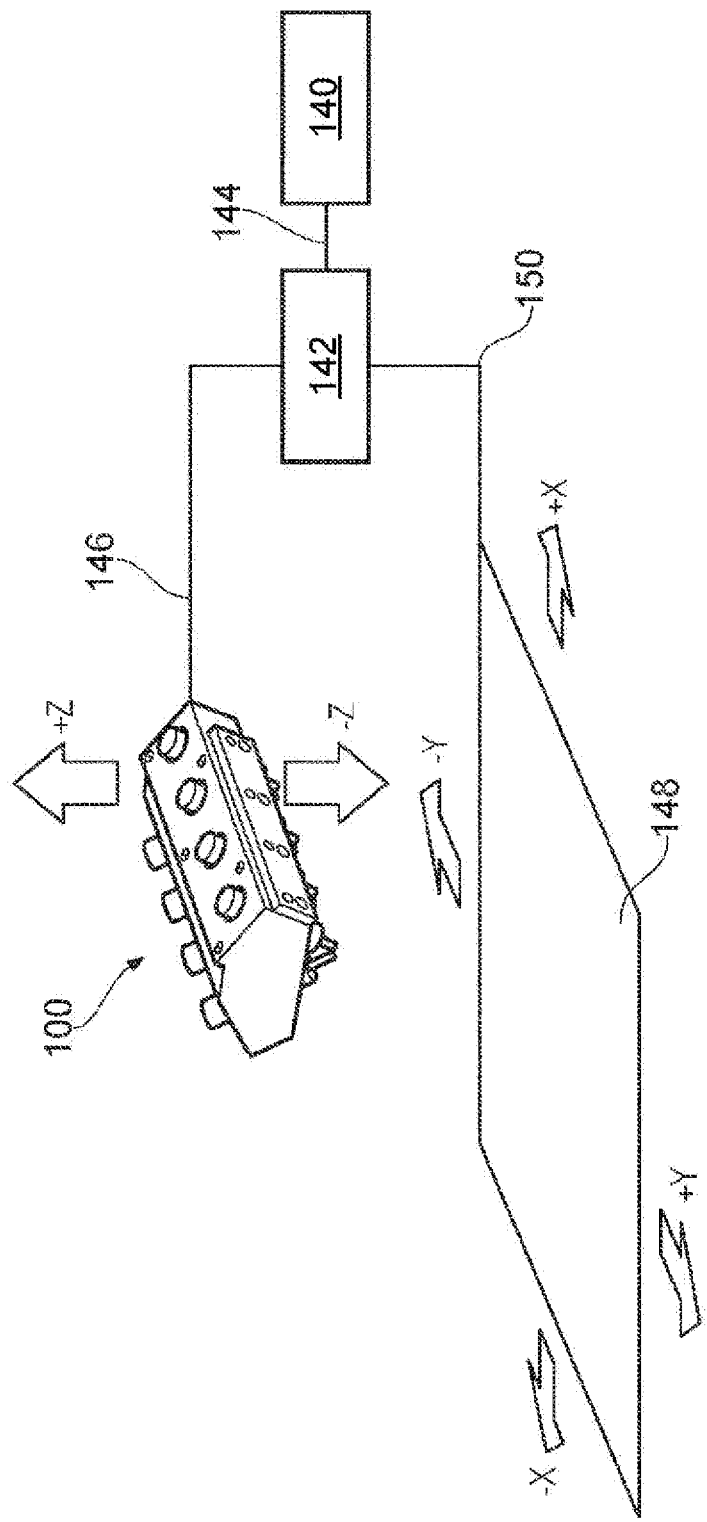
FIG. 3a illustrates an open loop control system for use with a printing apparatus.
Figure 3B:
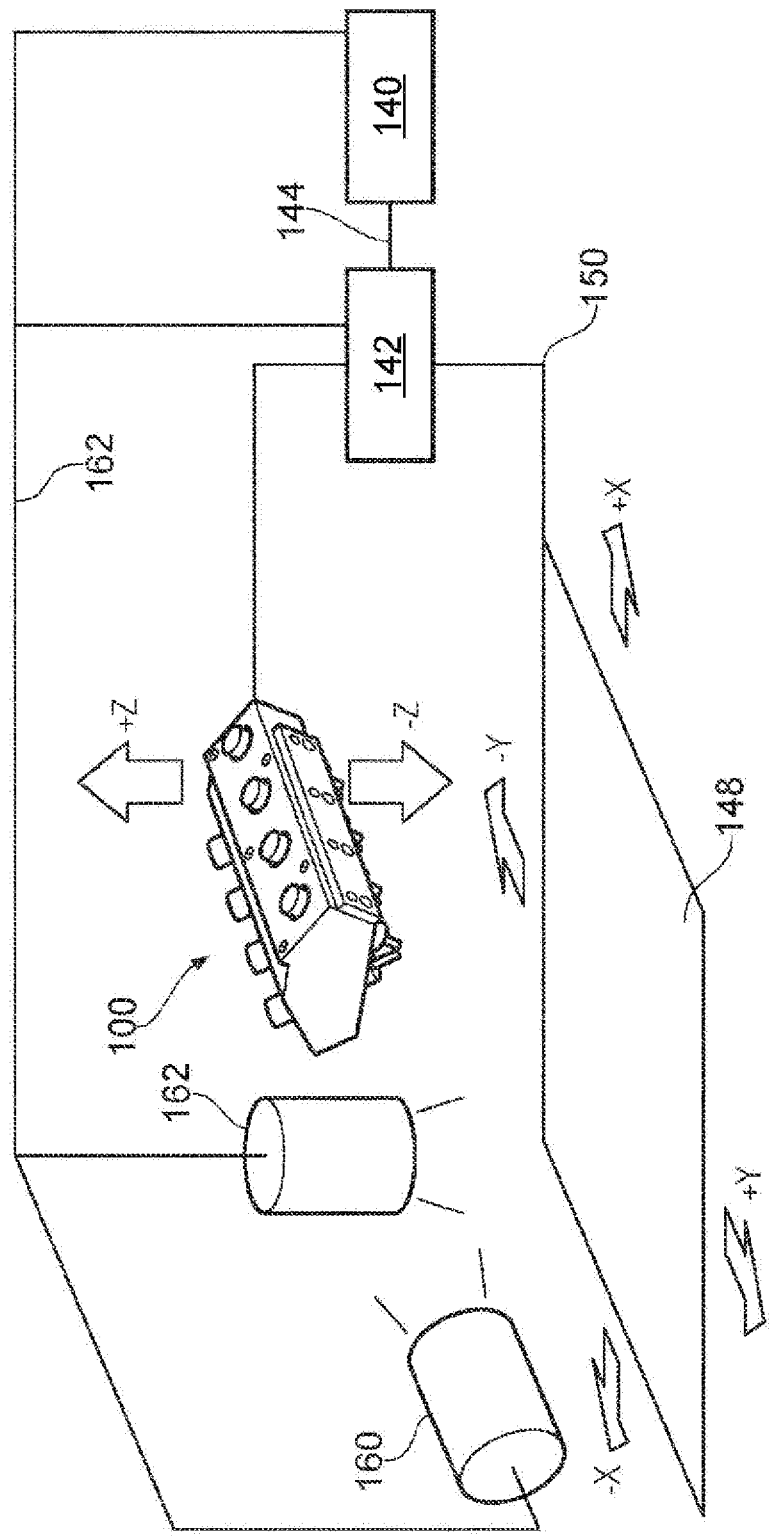
FIG. 3b illustrates a closed loop control system for use with a printing apparatus.

FIGS. 3a and 3b illustrate example control systems for controlling the jetting process for deposition onto a substrate 148. In these examples the software control 140 of a computer controls the position of printing apparatus in the X, Y, and Z axes in relation to the substrate. When a droplet is needed the software control 140 may issue a trigger to the printing apparatus. For example, the trigger may be issued by a transistor-transistor logic (TTL). The control system may either be open loop or closed loop.

FIG. 3a illustrates an open loop control system for use with a printing apparatus 100. In this example the printing apparatus has four pairs of jet actuators mounted within a jetting head. The TTL trigger issued by the software control 140 of the computer is sent to a controller 142 via a computer interface 144. Controller 142 distributes the trigger to an individual controller (not shown) for each jet actuator via synchronisation control line 146. The controller of each jet actuator adds the appropriate timing delay before opening the microvalve. Preferably, each valve is integrated with its own dedicated controller such that the timings of droplet deposition can be tailored to the specific dynamics of each valve to ensure optimum impingement. A feedback signal for the axis drive and position is fed via line 150 to controller 142.

FIG. 3*b* illustrates a further control system for use with printing apparatus 100. The control system shown in FIG. 3*b* includes corresponding features to the control system in FIG. 3*a* that for brevity will not be discussed again in detail. This control system differs from that shown in FIG. 3*a* in that it is closed loop. In the system shown in FIG. 3*b*, image processing feeds back the impingement efficiency using a jet imaging camera 160 and fiducial camera 162 along an image feedback line 164 and automatically adjusts jet timings of droplet deposition to optimise impingement of the first and second liquid droplets.

FIGS. 4-8*b* illustrate a second example of a printing apparatus 100 for impinging liquids from at least two liquid sources. The printing apparatus 100 includes four pairs of jet actuators. Each pair of jet actuators includes a first jet actuator 102 configured to dispense a first liquid from a first liquid source and a second jet actuator 104 configured to dispense a second liquid from a second liquid source. The apparatus 100 also includes an adjustment element 202 for each pair of jet actuators configured to adjust a trajectory of at least the first liquid dispensed from the first jet actuator. In this way, the trajectory of the first liquid may be adjusted such that the first liquid impinges the second liquid dispensed from the second jet actuator.

Figure 4:
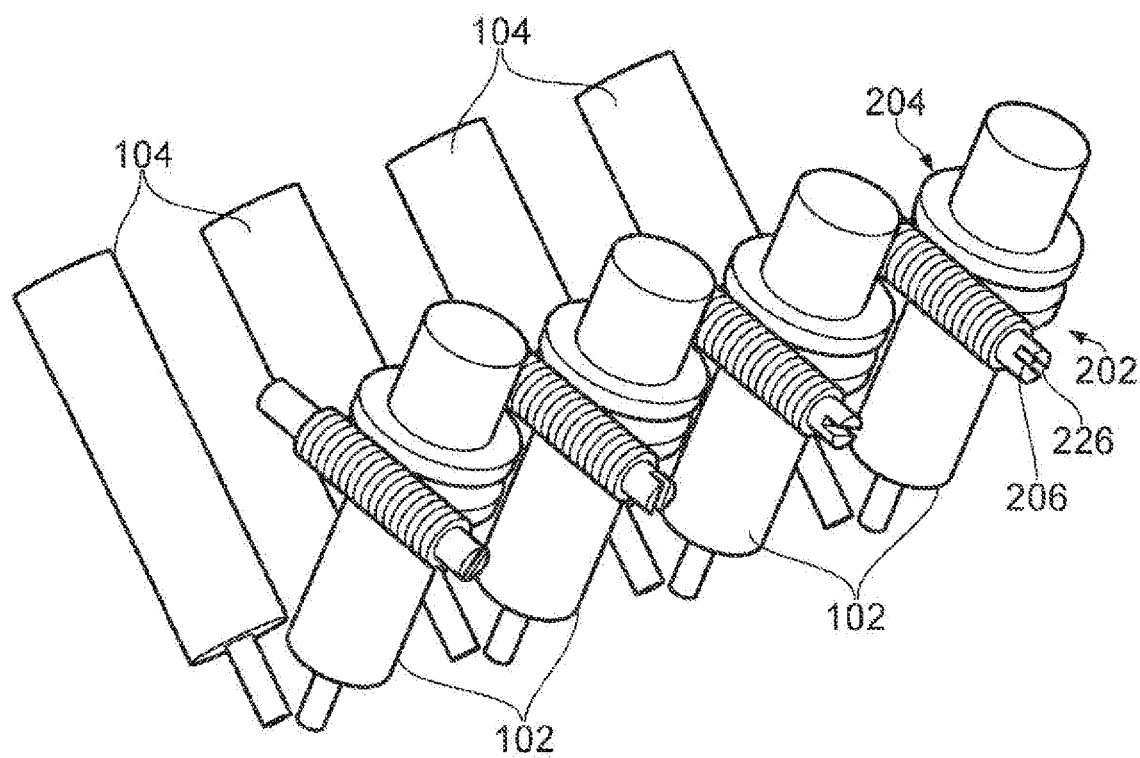
FIG. 4 illustrates a second example of a printing apparatus.
Figure 5:
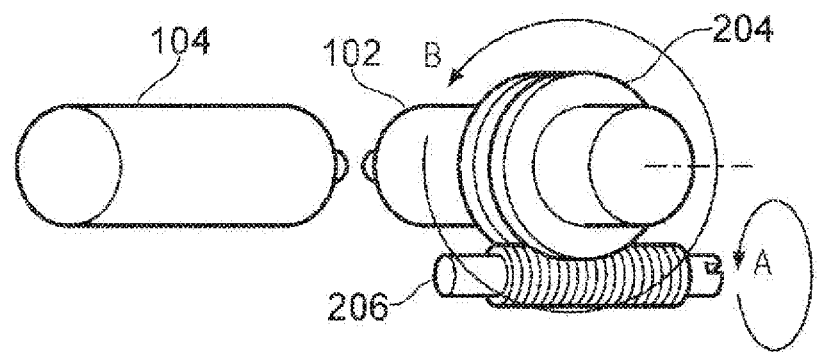
FIG. 5 illustrates another view of the adjustment element of the example shown in FIG. 4.

FIG. 4 illustrates four operational pairs of jet actuators (each including a first jet actuator 102 and a second jet actuator 104). In this example, the first jet actuator 102 of each operational pair, includes an adjustment element 202.

The adjustment element 202 is configured to adjust the position of the first jet actuator 102 relative to the second jet actuator 104. Adjusting the position of the first jet actuator thereby adjusts the trajectory of the first liquid dispensed from the first jet actuator.

The adjustment element 202 includes an actuating element for adjusting the position of the first jet actuator. In this example, the actuating element includes a threaded drive element 206, which interacts with a mounting collar 204. In this example the mounting collar 204 is a collet and the threaded drive element 206 is a worm drive.

As shown in FIGS. 5 and 6*a-c*, the first jet actuator 102 is eccentrically mounted in the collet 204. That is, the first jet actuator 102 is eccentrically mounted in the collet 204 with respect to a central axis of the collet 204. The actuating element 206 is configured to rotate the collet 204 to linearly adjust position of first jet actuator 102 with respect to the second jet actuator 104.

The outer surface of the worm drive 206 is threadably engaged with spurs on the outer surface of the collet 204 (the spurs are not shown). In this example, the worm drive 206 includes a grooved end 226 to assist in the application of a torque to the worm drive 206 and hence to assist in the rotation of the worm drive 206. In operation, the worm drive is rotated (as indicated by the arrow A in FIG. 5) causing the collet 204 to rotate around its central axis (as indicated by the arrow B in FIG. 5).

Control of the worm drive 206 may be via a controller, or in other examples the worm drive may be manually activated using a screw driver, for example. The worm drive 206 may be controlled using control systems as shown in FIGS. 3*a* and 3*b*. The control systems as shown in FIGS. 3*a* and 3*b* may thus control the release of the first and second liquids from the respective first and second jet actuators. The control systems as shown in FIGS. 3*a* and 3*b* may also (or alternatively) control the position of at least the first jet actuators, to thereby optimise impingement of the first and second liquids.

Figures 6A, 6B, 6C:
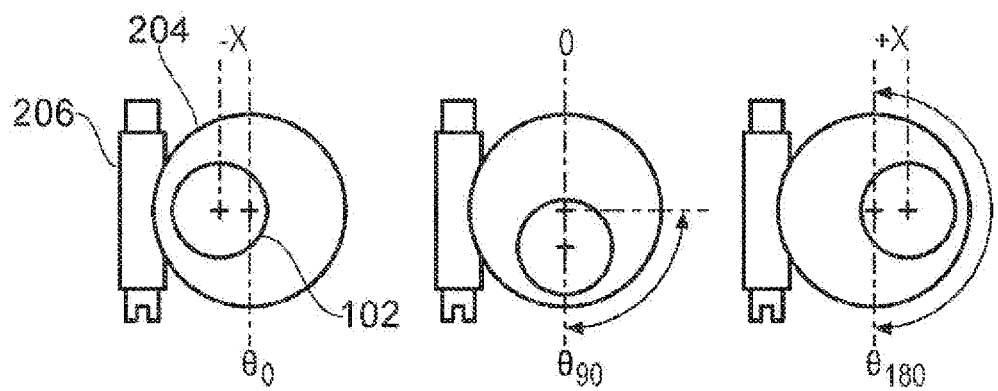
FIGS. 6a-6c illustrates a plan view of the adjustment element of the example shown in FIG. 4.

FIGS. 6*a*-6*c* illustrate the relative positions of the collet 204 and the first jet actuator 102 after the collet 204 is rotated through an angle of 0, 90 and 180 degrees respectively. The rotation of the collet 204 acts to rotate the central axis of first jet actuator 102 around the central axis of the collet, as shown in FIGS. 6*a*-6*c*. In doing so, the rotation of the collet 204 acts to shift the central axis of the first jet actuator 102 relative to the central axis of the corresponding second jet actuator 104.

In this example the adjustment element 202 is configured to effect translational movement of the first jet actuator 102 with respect to the second jet actuator. That is, the first jet actuator 102 is translated, such that the position of the second end $102_2$ of the first jet actuator 102 is altered relative to the position of the second end $104_2$ of the second jet actuator 104. The position of the first jet actuator 102 may be adjusted to help ensure that drops of liquid dispensed from the first jet actuator impinge with drops of liquid dispensed from the second jet actuator 104. In this example, the angle from which drops of liquid are dispensed from the first jet actuator remains unchanged as the position of the first jet actuator is adjusted. In other words, the angular orientation of the first jet actuator remains fixed.

The eccentricity (X) of the central axes of the first jet actuator 102 and the collet 204 is preferably between 25 μm and 1 mm More preferably, the eccentricity is around 150 μm. With an eccentricity of 150 μm the total (nonlinear) adjustment that can be achieved is 300 μm.

In use, the position of the first jet actuator may be adjusted by rotation of the worm drive 206, which causes rotation of the collet 204. The rotation of the collet 204 allows fine adjustment of the position of the first jet actuator with respect to the second jet actuator. In this way, the position of the first jet actuator can be optimised to suit the properties of the first and/or second liquids to help ensure that the trajectories of the liquids meet and the liquids impinge.

Figure 7:
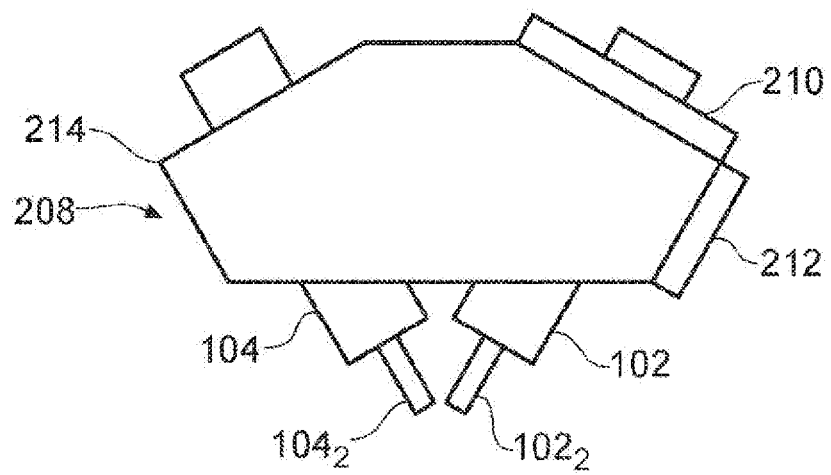
FIG. 7 illustrates the printing apparatus of FIG. 4 mounted within a jetting head.
Figure 8A:
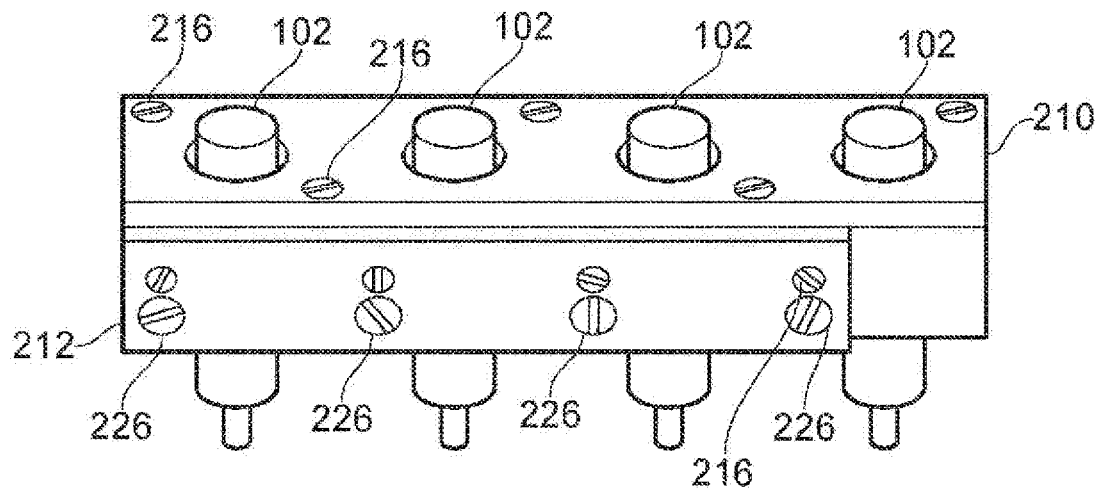
FIGS. 8a and 8b illustrate side and top views respectively of the mounted printing apparatus as per FIG. 7.
Figure 8B:
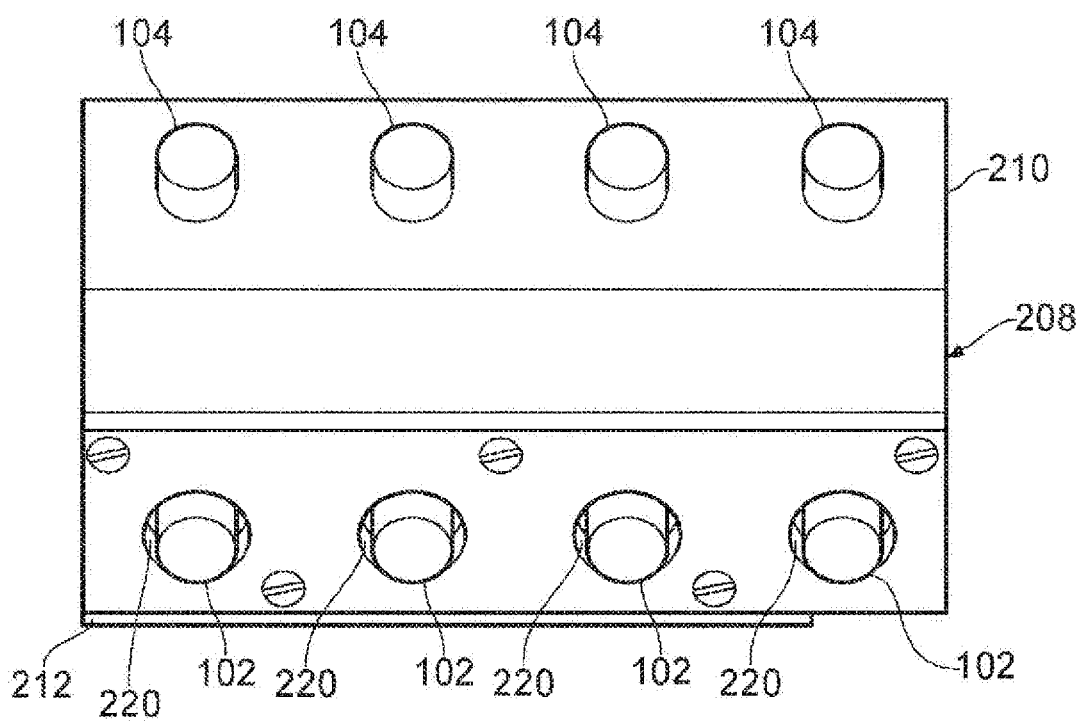

FIGS. 7, 8*a* and 8*b* illustrate the four operational pairs of jet actuators and corresponding adjustment elements, mounted within jetting head 208. In this example, the jetting head 208 includes a body portion 214, a top plate 210 and a side plate 212.

As shown in FIGS. 8*a* and 8*b* in this example the top plate 210 is attached to the body portion 214 by screws 216, although any other suitable means of attachment may be used, for example a suitable adhesive. The top plate 210 includes circular orifices 220 to receive the first end of the first jet actuators. The diameter of the orifices is larger than that of the first jet actuators 102 to allow space for the first jet actuators 102 to rotate around the central axis of the collet 204.

The side plate 212 is mounted on a side of the jetting head 208 and allows access to the grooved end 226 (or head) of the worm drive 206 from outside the jetting head 208. Similar to the upper plate 210, the side plate 212 is attached to the body portion by screws 216, though other suitable attachment means may alternatively be used.

It will be appreciated that the timing of the liquid droplets dispensed from the first and second jet actuators may also be controlled to help ensure the first and second liquid droplets impinge. For example, where the first and second liquids have substantially the same rheological properties, the first and second liquid droplets may be dispensed substantially simultaneously. In other examples, where the first and second liquids have different properties, there may be time lag between the two liquids being dispensed. As discussed above, a controller, which may be part of the control system of FIGS. 3a-3b, may control the timing of the droplets dispensed from the first and second jet actuators. A single controller may control the valves of all of the jet actuators or each jet actuator may have a separate controller associated with it.

In this example, the first liquid comprises a first gel precursor and the second liquid comprises a second gel precursor. For example, the first gel precursor may be a relatively low viscosity Sodium alginate and the second gel precursor may be a calcium chloride. These particular gel precursors can combine to form a polysaccharide Alginate hydrogel. In another example, the first liquid may be a low viscosity solution of fibrinogen and the second liquid may be a low viscosity solution of thrombin. These liquids can combine to form a protein fibrin gel.

Figure 9:
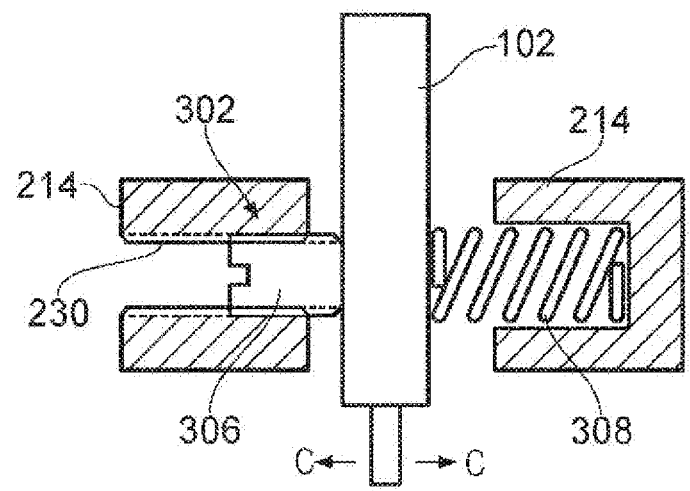
FIG. 9 illustrates another example of an adjustment element.

FIG. 9 illustrates a further example of an adjustment element 302. In this example the actuating element for adjusting the position of the first jet actuator 102 is grub screw 306.

The grub screw 306 is threadably engaged with a channel 230 situated within the body portion 214 of the jetting head. In operation, as the grub screw is turned, the first jet actuator 102 is displaced linearly by a distance relative to the pitch of the grub screw 306 multiplied by its rotation. That is, the grub screw 306 is used to apply a force to move the first jet actuator 102 laterally in the jetting head, in the direction of arrows C.

In this example, the adjustment element 302 further comprises a biasing element 308 arranged to oppose the force of the actuating element (grub screw) on the first jet actuator. In this example, the biasing element 308 is a spring, although any suitable biasing element may be used.

The spring 308 is housed within a recess in the body portion 214 of the jetting head. The spring 308 provides a counteracting force to the force applied to the first jet actuator 102 by the grub screw 306, which allows for adjustment while supporting the first jet actuator 102 securely in a substantially fixed orientation.

As with the first example of an adjustment element 202, in this example the adjustment element 302 is configured to effect translational movement of the first jet actuator 102 with respect to the second jet actuator as indicated by the arrows C.

In the same manner as the previous example, the adjustment element 302 may further include a controller (not shown) to control the actuating element (grub screw).

Figure 10:
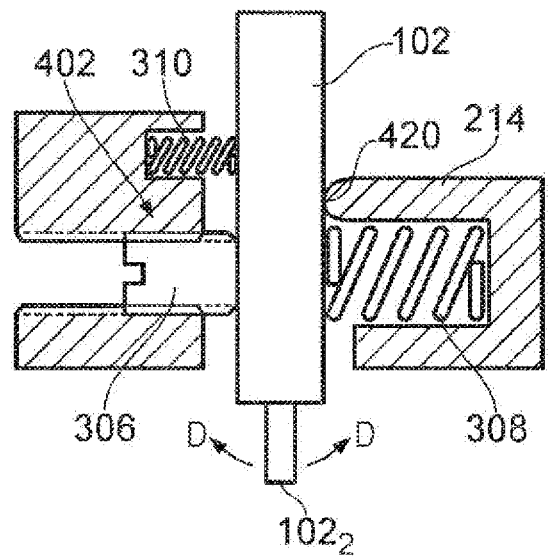
FIG. 10 illustrates another example of an adjustment element.

FIG. 10 illustrates a further example of an adjustment element 402. Similar to the previous example of FIG. 9, the actuating element for adjusting the position of the first jet actuator 102 is grub screw 306 and the adjustment element 402 further includes a biasing element 308 arranged to oppose the force of the grub screw 306 on the first jet actuator 102.

However, in this example, the adjustment element is configured to effect rotational movement of the first jet actuator 102.

The adjustment element 402 further includes a further biasing element 310 arranged to apply a force to the first jet actuator 102 to control rotational movement of the first jet actuator upon actuation of the actuating element.

In this example, the grub screw 306 adjusts the first jet actuator's position and a further biasing element 310 ensures that it remains in contact with a fulcrum 420. In this example, the fulcrum 420 is an extension of the edge of the recess within which the biasing element 308 is housed. In other examples the fulcrum may be a separate element coupled to the housing. In this example the further biasing element 310 is a spring, although any suitable biasing element may be used.

As the first jet actuator 102 is displaced by the grub screw, the second end $102_2$ of the first jet actuator 102 moves in an arc about the fulcrum 420. The use of a fulcrum 420 to support the first jet actuator 102 may allow for finer and more stable adjustment.

Figure 11:
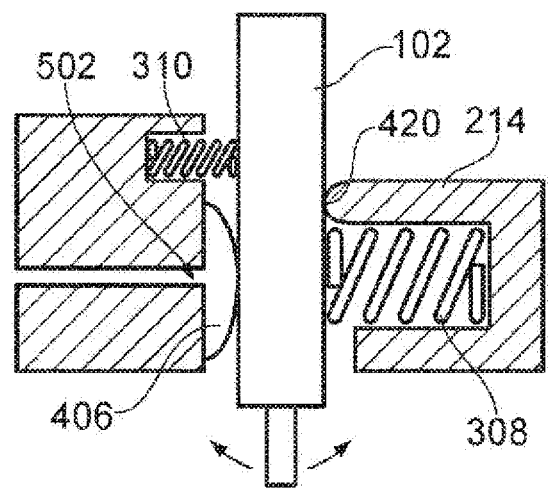
FIG. 11 illustrates another example of an adjustment element.

FIG. 11 illustrates a further example of an adjustment element 502. In most respects the adjustment element 502 has corresponding features to the adjustment element 402 of FIG. 10.

However, in contrast to the previous example, the actuating element for adjusting the position of the first jet actuator 102 is diaphragm 406. The diaphragm may be a pneumatic or hydraulic diaphragm. The degree of adjustment is an interaction of the spring stiffness, the surface area of the actuator and the pneumatic or hydraulic pressure applied.

Figure 12:
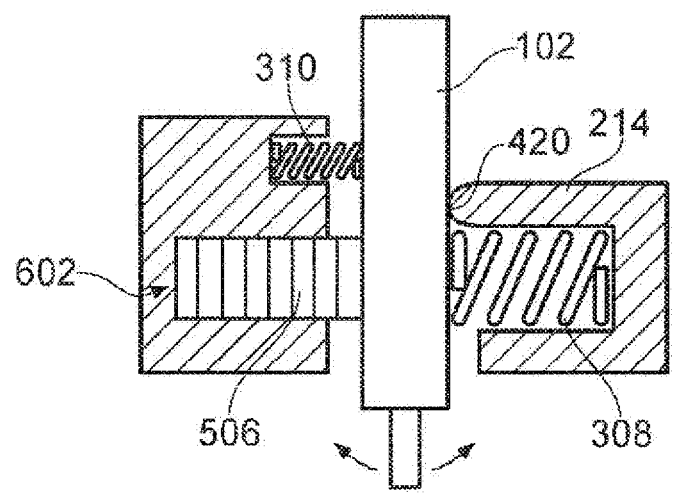
FIG. 12 illustrates another example of an adjustment element.

FIG. 12 illustrates a further example of an adjustment element 602. In most respects the adjustment element 602 has corresponding features to the adjustment element 402 and 502 of FIGS. 10 and 11 respectively. However, in this example the actuator for adjusting the position of the first jet actuator 102 is a piezo actuator 506.

The piezo actuator 506 can come in several forms including a piezo disc stack (as in the example shown in FIG. 12) where the degree of adjustment is relative to the potential difference across the piezo stack. Alternatively, the piezo actuator may be a piezo stepper motor, in which piezo beam arrays bend under applied voltages and act to move a rod actuator through peristalsis. In another example, the piezo actuator may be a deformable piezo ring, which may deform relative to an applied voltage.

Figure 13:
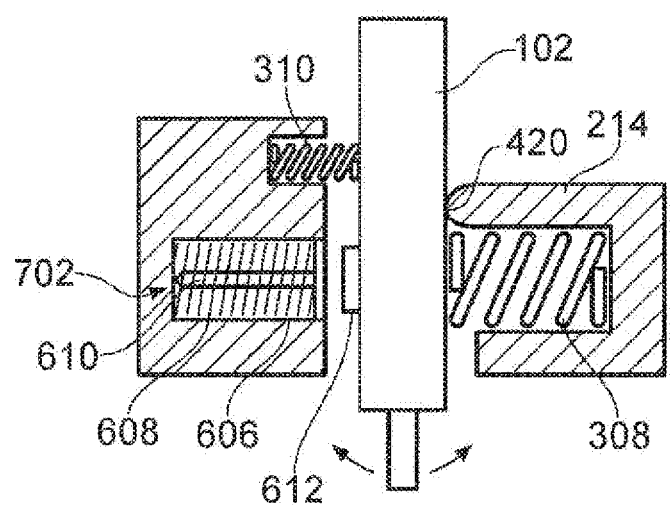
FIG. 13 illustrates another example of an adjustment element.

FIG. 13 illustrates a further example of an adjustment element 702. As with the previous example, in most respects the adjustment element 702 has corresponding features to the adjustment element 402, 502 and 602 of FIGS. 10-12. However, in this example the actuator for adjusting the position of the first jet actuator 102 is an electromagnet 606.

The electromagnet 606 includes coil windings 608 and an iron core 610. The electromagnet 606 interacts with a permanent magnet 612 mounted on the first jet actuator. The electromagnet 606 and permanent magnet 612 are mounted in opposing positions. The degree of adjustment of the first jet actuator is controlled by the voltage applied to the electromagnet's windings, the stiffness of the spring 308 and the displacement of the permanent magnet from the electromagnet's iron core.

Figure 14:
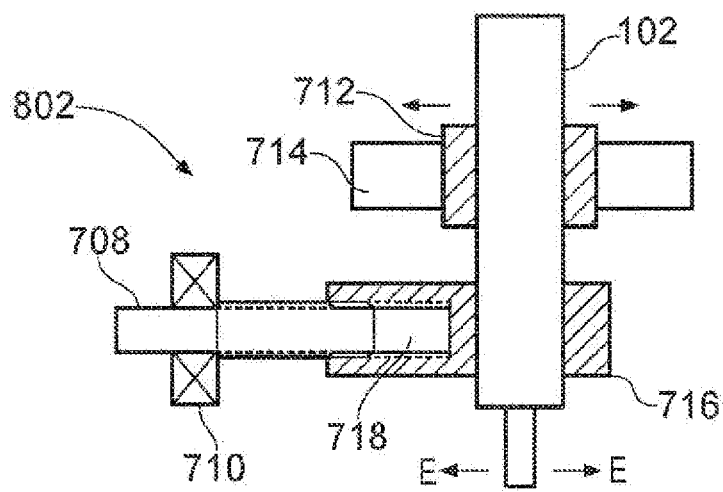
FIG. 14 illustrates another example of an adjustment element.

FIG. 14 illustrates a further example of an adjustment element 802. In this example the adjustment element 802 is configured to effect translational movement of the first jet actuator 102 with respect to the second jet actuator.

The adjustment element 802 includes an actuating element for adjusting the position of the first jet actuator 102. In this example the actuating element is an adjustment screw 708 attached to a constrained bearing 710. The adjustment screw 708 is threadably engaged with a channel 718 of actuator housing 716, which is mounted on first jet actuator 102.

The first jet actuator 102 is mounted on a linear bearing carriage 712, which is slidable along rail 714. Rail 714 is attached to the body 214 of the jetting head (this attachment is not shown).

In operation, as the adjustment screw 708 is laterally constrained by bearing 710, when the adjustment screw is turned the actuator housing 716 is drawn towards/pushed away from the constrained bearing 710. As such, the first jet actuator 102 is moved laterally in the direction of either of the arrows E. The degree of adjustment is relative to the pitch of the screw multiplied by its fraction of rotation.

As discussed with regards to previous examples (for example adjustment element 302) control of the adjustment screw 708 may be via a controller, or in other examples the adjustment element may be manually activated using a screw driver, for example.

Figure 15:
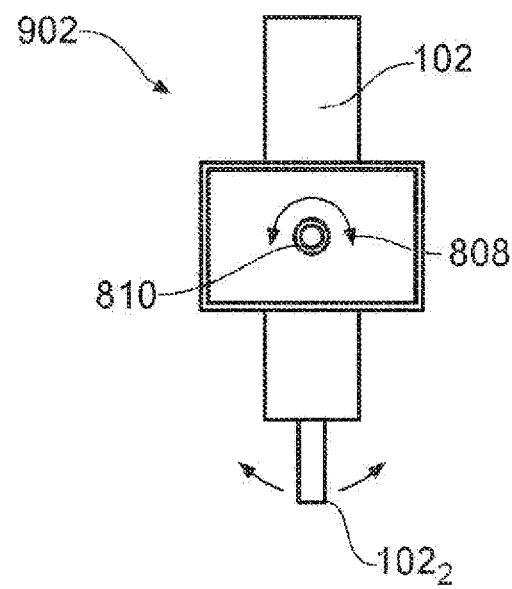
FIG. 15 illustrates another example of an adjustment element.

FIG. 15 illustrates a further example of an adjustment element 902. In this example the adjustment element 902 is configured to effect rotational movement of the first jet actuator 102.

In this example, the actuating element for adjusting the position of the first jet actuator is gimbal 808. The first jet actuator 102 is mounted on gimbal 808.

Alignment is achieved by rotating the gimbal around centre of rotation 810, which results in the movement of the second end 102₂ of the first jet actuator 102 in an arc relative to the centre of rotation 810 of the gimbal. The degree of adjustment is product of the angular displacement of the gimbal and the distance from the axis of rotation to the second end 102₂ of the jet actuator 102.

The rotation of the gimbal may be controlled via a controller or alternatively may be controlled manually.

Figure 16:
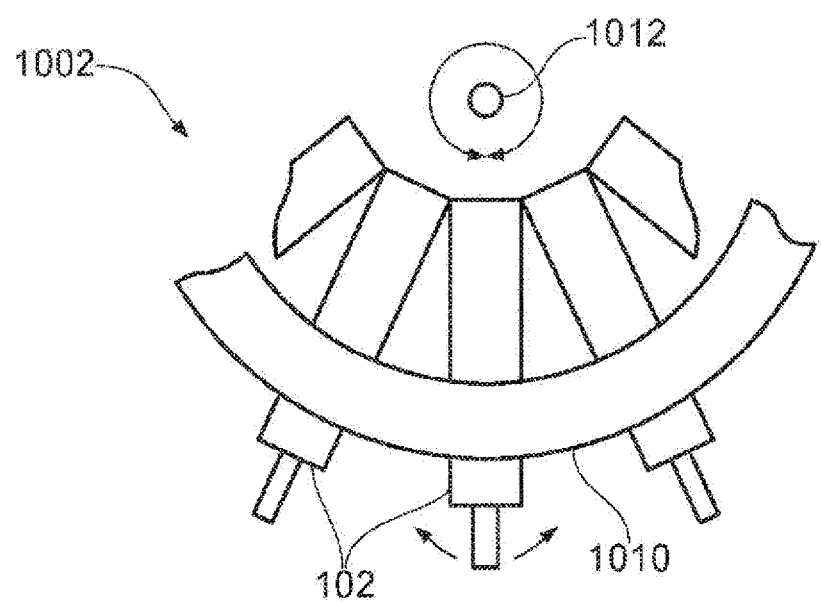
FIG. 16 illustrates another example of an adjustment element.

FIG. 16 illustrates a further example of an adjustment element 1002. In this example the adjustment element 1002 is configured to effect rotational movement of the first jet actuator 102.

In this example, a plurality of first jet actuators 102 are mounted on a frame 1010, which in this example is a capstan.

In this example, the actuating element for adjusting the position of the first jet actuator is a stepper or a servo motor, which rotates the capstan around its central axis 1012. The degree of adjustment is relative to the angular displacement of the capstan and the distance between the rotational axis and the second end 102₂ of the jet actuator 102.

In this example each of the plurality of jet actuators 102 mounted on the frame 1010 may contain different liquids. This may be particularly useful where the material to be formed can change. For example, a fibrin gel structure may be constructed with fibrinogen having different cells types. Rather than having multiple pairs of jet actuators, the capstan arrangement may be used and each of the jet actuators mounted on the capstan may contain or be coupled to different liquid sources having different cell types. The capstan may then be rotated to select the desired jet actuator.

The rotation of the capstan may be controlled via a controller or alternatively may be controlled manually.

Figure 17:
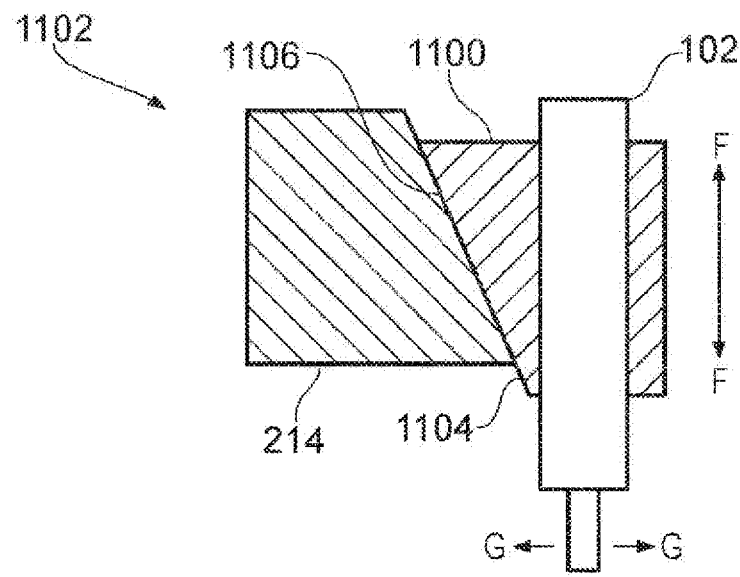
FIG. 17 illustrates another example of an adjustment element.

FIG. 17 illustrates a further example of an adjustment element 1102. In this example the adjustment element 1102 is configured to effect translational movement of the first jet actuator 102 with respect to the second jet actuator.

In this example, the first jet actuator is mounted in head mount 1100. A face 1104 of the head mount 1100 is slidably engaged with a corresponding face 1106 of the body portion 214 of the jetting head.

Alignment is achieved by the displacement of the head mount 1100 in a first direction (indicated by arrows F). The slidably engaged faces 1104,1106 are orientated relative to said first direction in such a way that as face 1104 slides along face 1106, the head mount 1100 is also displaced in a second direction (indicated by arrows G). Hence the displacement of head mount 1100 in a first direction also results in the displacement of the first jet actuator 102 in a second direction (indicated by arrows G). In this example the first and second directions are substantially perpendicular.

In this example, the first jet actuator 102 may also be adjustable within head mount 1100. As such, the first jet actuator 102 may be moved within head mount 1100 to compensate for any movement of the head mount 1100 in the first direction F. In this manner the first jet actuator 102 may be kept at a consistent level with second jet actuator 104.

In this example, the actuating element for adjusting the position of the first jet actuator is a grub screw or a lead screw (not shown).

The movement of the head mount 1100 may be controlled by a controller or alternatively may be controlled manually.

Figure 18:
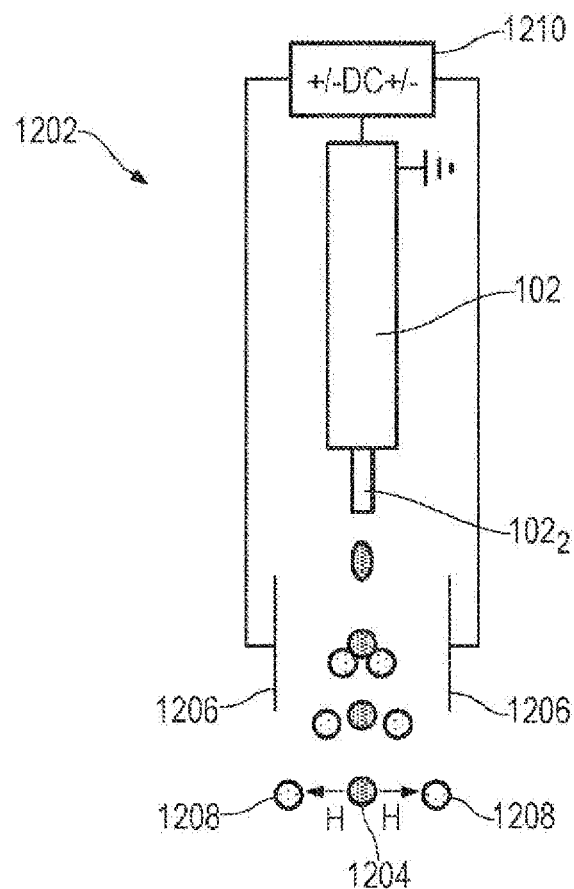
FIG. 18 illustrates another example of an adjustment element.

FIG. 18 illustrates a further example of an adjustment element 1202. The adjustment element 1202 is configured to apply a force to the first liquid after it is dispensed from the first jet actuator 102 to adjust the trajectory of the first liquid. This adjustment element 1202 may be used as an alternative or in combination with any of the adjustment elements described above.

In this example, the adjustment 1202 element includes electrically charged deflection plates 1206 for applying an electrostatic force to the first liquid. In this example the deflection plates 1206 are parallel plate electrodes, which may be made from any suitable conductive material (for example stainless steel, copper aluminium, brass, carbon) and are charged by a DC voltage source 1210.

The charged deflection plates are positioned adjacent to the second end 102₂ of the first jet actuator 102. An appropriate potential difference is applied across the plates by battery 1210 or other suitable power source. As the droplet (s) enter the electric field created by the potential difference between the plates 1206, a lorentz force is present on the droplet and thereby changes the trajectory of that droplet.

FIG. 18 illustrates the path of a droplet 1204 without the application of an electric field. The trajectory of droplets 1208 have been shifted in the direction of arrows H by the application of an electric field.

The degree of adjustment is related to the strength of the electric field, which is dictated by the potential difference applied across the plate electrodes. To increase the influence on the droplets trajectory or to change the direction of the deflection, the potential difference is increased or the polarity reversed respectively.

Each of the examples described herein may be used in a 3D printing method, and may be particularly suitable for 3D bioprinting. In use, the first and second jet actuators are provided with first and second liquids respectively. The liquids may be fed to the jet actuators from respective liquid sources or the liquid sources may be reservoirs within each respective first and second jet actuator.

The first jet actuator is aligned with the second jet actuator via the adjustment element so that liquid droplets dispensed from each jet actuator have intersecting trajectories. In this way, the liquid droplets can impinge when dispensed.

The control system controls release of the first and second liquids from the first and second jet actuators to release the liquids in droplet form (drop-on-demand) The controller times the release of the droplets such that the first and second liquid droplets impinge and combine mid-air. The combined droplet falls to and is thereby deposited on the substrate to form part of a 3D printed structure.

The control system may control the position of the printing (jetting) head with respect to the substrate so that further combined droplets may be deposited on the substrate to further build up the 3D printed structure.

Various modifications to the detailed arrangements as described above are possible.

The example apparatus described herein may each be suitable for three-dimensional bioprinting.

The control system described in relation to FIGS. 3a-3b may be suitable for controlling any of the embodiments described above.

The above examples describe the alignment of two jet actuators, such that the droplets produced impinge to form a single droplet. Such apparatus are not limited to the interaction of just two droplets and could conceivably be applied to any plurality of jet actuators (e.g. alignment of three or more jet actuators).

Although in the examples described above, the first and second liquids include gel precursors, other liquids may also be used.

For example, at least one of the first and second liquids may include a reactive polymer precursor. The reactive polymer precursors may combine and react on impingement to form a polymer that may be deposited on the substrate.

Generally, liquids including gel precursors may include biological materials, for example cells, and may be used for bioprinting. Biological materials (cells or biomolecules) may be premixed within a gel precursor (e.g. sodium alginate or fibrinogen) and then impingement printed onto a substrate to form 3D structures, which are then matured in vivo or in vitro into functional tissues.

It will be appreciated that other actuating elements different to those described in the specific examples above may also be suitable for adjusting the position of at least one of the jet actuators. For example, linear, rotational or pivotal movement of the actuating element may apply a suitable force to at least one of the jet actuators to thereby adjust the position of the jet actuator.

It will be appreciated that the jetting head described above in relation to FIGS. 8a and 8b may be suitably modified to accommodate an array of any jet actuators and any of the adjustment elements described herein.

With the above-described examples, the printer configuration allows for easier variability in viscosity of the liquids used in the printer. The printer can be adjusted to accommodate for variations in viscosity. For example, the position of at least one of the jet actuators may be adjusted, the trajectory of the droplets as they exit the jets may be adjusted or the timings of the deposition of the droplets in each jet actuator may be controlled to ensure that the droplets trajectories meet (intersect) and the droplets impinge. Any combination of these adjustment methods may be used.

Each of these adjustment methods allow for fine adjustment of the trajectories of the liquid droplets exiting the jet actuators. The adjustment is on the micron scale and can allow adjustments of around 0 to 150 µm.

Thus, the printer configuration can provide more consistent printing of materials since the impingement of the liquids can be accurately controlled.

The energy imparted to a droplet by a jet actuator is conserved through the impingement process meaning that if a droplet impinges a droplet of higher velocity or mass, the resultant combined droplet will proceed with a bias towards the direction of the higher energy droplet. It may be necessary to have unequal masses or velocities of droplets to ensure the combined droplet remains in the intended path depending on the material being processed.

Alternatively or in addition, other mechanisms may be used to ensure the combined droplet remains in the intended path. For example, the control system may include a feedback and velocity (pressure) optimisation control. Alternatively or in addition, the jet actuators may tilt (e.g. by actuating elements of FIG. 10-13, 15 or 16). This helps to adjust the initial direction of motion of the droplet to account for any bias effect upon impingement. Alternatively or in addition, a pneumatic jet may be used, which can apply a highly controlled jet of air to change the trajectory of the droplet. Alternatively or in addition, an electric field may be used (in a similar manner to the example of FIG. 18) to maintain the combined droplet in the intended path.

The examples described above also provide improved reliability. By using lower viscosity precursors that react on impingement, the liquids are less likely to gelate in the jet actuators and therefore clogging of the jet actuators can be significantly reduced or prevented. By using lower viscosity liquids in the jet actuators, the liquids can be deposited faster than higher viscosity liquids, and so the speed of the printing process can be significantly increased.

The examples described above can be scaled up for larger scale printing requirements by increasing the number of pairs of jet actuators within the printing head to form an array of impinging jets. Each pair of jet actuators may deposit the same liquids allowing for faster printing of a single material. In other examples, at least one of the pairs of jet actuators may deposit different liquids compared to the other jet actuators. This may allow for simultaneous printing of different materials, thus increasing the printing efficiency. In some examples, the printing process may be tens of times faster or more than previously known methods.

Figure 19:
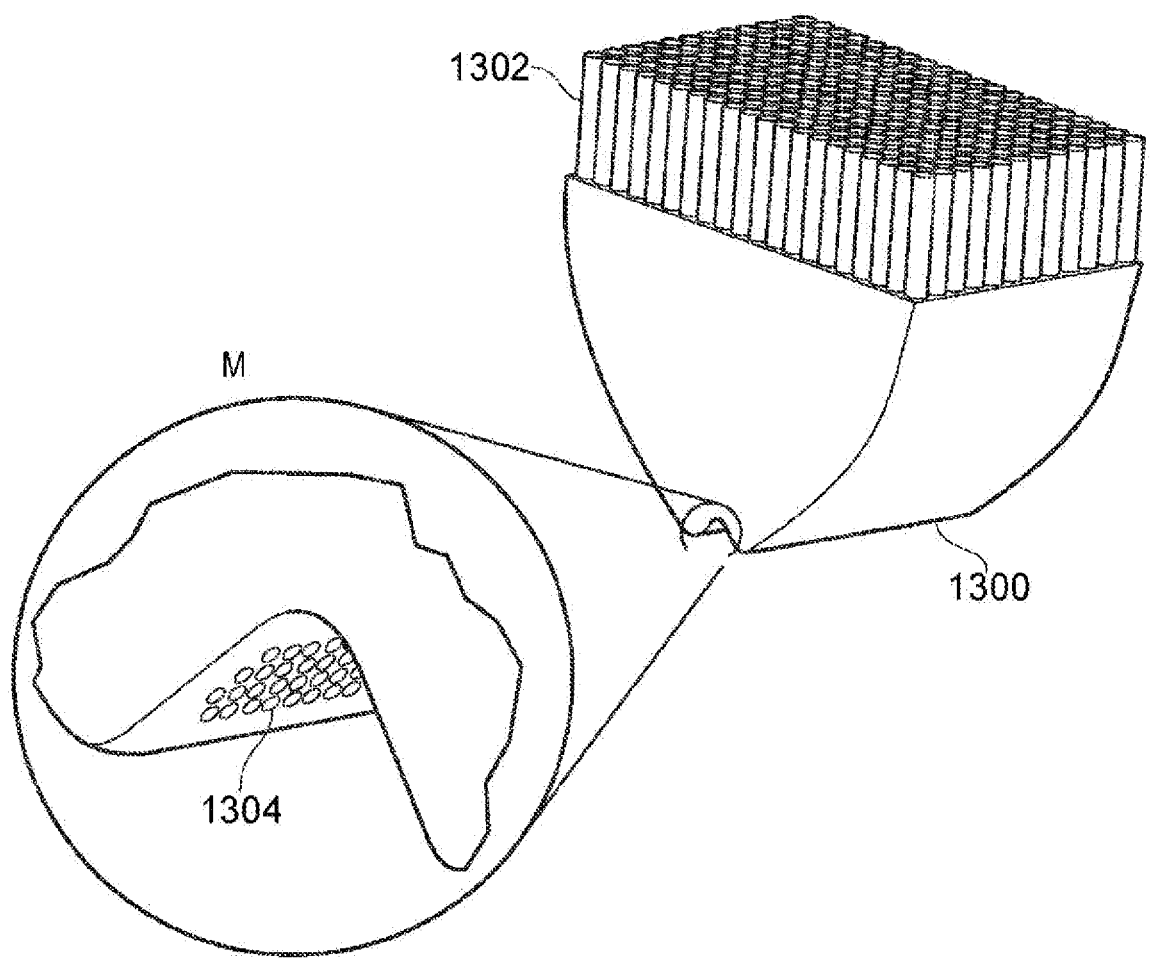
FIG. 19 illustrates a large scale jetting array.

While jetting heads designed for R&D would be expected to use alignment mechanisms to optimise for uncharacterised materials, large compact jetting arrays may not need the facility for post-manufacture alignment as the jetting heads could be aligned during the manufacturing process. These heads could be designed for specific materials and intended for high throughput. FIG. 19 illustrates a large compact jetting array 1300, including control valves 1302. The magnified view, M, shows a detailed view of the jet micro-array 1304.

Each pair of jet actuators in the array may have at least one jet actuator of which the position is independently adjustable. In this way, impingements of the liquids from each pair of jet actuators in the array can be separately adjusted.

Suitably, the printing apparatus of the invention may have utility in bioprinting. In this regard, either the first, second or both of the jet actuators may be configured to dispense a liquid comprising viable cells. Hence, the printing apparatus of the invention may be used to produce biological materials (such as gels comprising biological cells).

Suitably, either the first, second or both of the jet actuators may be configured to dispense a gel precursor (e.g. sodium alginate or fibrinogen) comprising cells or biomolecules, which may be printed onto a substrate to form 3D structures, which are then matured in vivo or in vitro into functional tissues.

Advantageously, the present invention provides use of the printing apparatus of the present invention to bioprint. For example, the bioprinting apparatus can be used to print 3D structures (e.g. gels) having a higher concentration of viable cells achieved using syringe based bioprinting systems. Hence, the printing apparatus of the invention may provide greater flexibility of cell density for bioprinting applications.

Accordingly, implementations of the present invention can provide use of the printing apparatus according to certain embodiments to produce a gel comprising viable cells, optionally at a concentration of 10 million to 90 million cells per ml of liquid precursor.

In another aspect, the present invention also provides a method of preparing a gel comprising viable cells. In some embodiments, the method comprises: 3D printing the gel using the apparatus of the invention wherein either the first or second jet actuator is configured to dispense a liquid comprising viable cells and the first and second liquid combine to form a gel.

In another aspect, the present invention further comprises a method of preparing a gel comprising viable cells. In some embodiments, the method comprises a method of 3D printing, wherein either the first and/or second liquid comprises viable cells and the liquids combine to form a gel.

In each of the above methods and uses, 3D structures (e.g. gels) may be formed comprising cells or biomolecules at a concentration of: at least 5 million cells per mL; or at least 10 million cells per mL; or at least 15 million cells per mL; or at least 20 million cells per mL; or at least 25 million cells per mL or at least 30 million cells per mL; or at least 40 million cells per mL; or at least 150 million cells per mL; or at least 60 million cells per mL; or at least 70 million cells per mL or at least 80 million cells per mL.

In each of the above methods and uses, 3D structures (e.g. gels) may be formed comprising cells or biomolecules at a concentration of between: 5 to 90 million cells per mL; or 10 to 90 million cells per mL; or 15 to 80 million cells per mL; or 20 to 60 million cells per mL; or 25 to 50 million cells per mL; or 30 to 40 million cells per mL. Suitably, such gels may be formed with the need for either a pre or post deposition crosslinking step.

The printing apparatus of the invention allows gels of such concentrations of viable cells to be produced within viscous gels such as CAF (collagen-alginate-fibrin).

The present invention can further provide gel comprising cells (e.g. viable cells) at any of the concentrations disclosed herein. Such gels may be produced using the apparatus of the invention or by the methods of the invention.

The gels may comprise mesenchymal stromal cells and the gel may be collagen-alginate-fibrin. Suitably, the gel may comprise collagen, alginates, fibrin or combinations thereof.

The type of gel is selected according to the use for the gel and will vary according to the cells being printed. For example, when the cells are mesenchymal stromal cells, the gel may be collagen-alginate-fibrin.

The inventors have surprisingly found that higher concentrations of cells (e.g. 40 million per mL) that can be bioprinted in accordance to some embodiments of the present invention can have advantageous effects in cell culturing and differentiation processes. For example, higher concentration of cells can result in increased speed of maturation of desirable cells during a cell differentiation process and may increase the speed at which desirable micro-tissues can be made.

One example, of such desirable properties is illustrated below. However, this can be seen to be illustrative of the general application of the advantages of using the printing apparatus according to some embodiments of the present invention in generating tissues.

Figure 20:
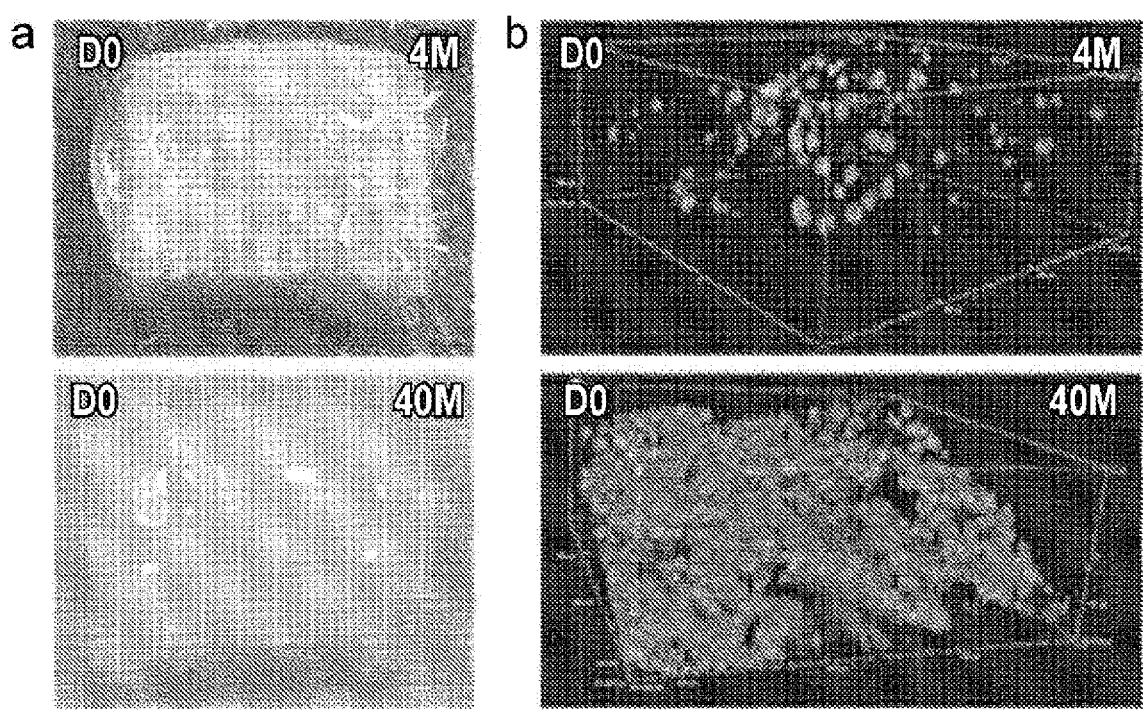
FIG. 20 illustrates the cell number, viability and functionality of CAF gels loaded with two different concentrations of mesenchymal stromal cells.

FIG. 20 shows the cell number, viability and functionality of two cell filled gels deposited using a printing apparatus according to some embodiments of the present invention. FIG. 20a is Stereomicroscope pictures showing the morphology of the CAF gels loaded with $4 \times 10^6$ cells/mL (top) and $40 \times 10^6$ cells/mL (bottom) immediately after printing. Scale bar represents 200 mm b Confocal microscopy volume stack showing cell distribution in CAF gels with different cell number. Scale bar represents 200 µm. The upper gel was created using a concentration of 4 million cells per mL of liquid precursor, the lower gel created using a concentration of 40 million cells per mL. Here the gels are collagen-alginate-fibrin (CAF), and the cells are mesenchymal stromal cells, with the cell filled gels cultured over a two week period in osteogenic media to induce the differentiation of cells towards osteoblasts, and the formation of bone neo-tissue. FIG. 20b confirms the cell densities by confocal microscopy volume stack showing cell distribution in CAF gels with different cell number. Scale bar represents 200 µm.

Figure 21:
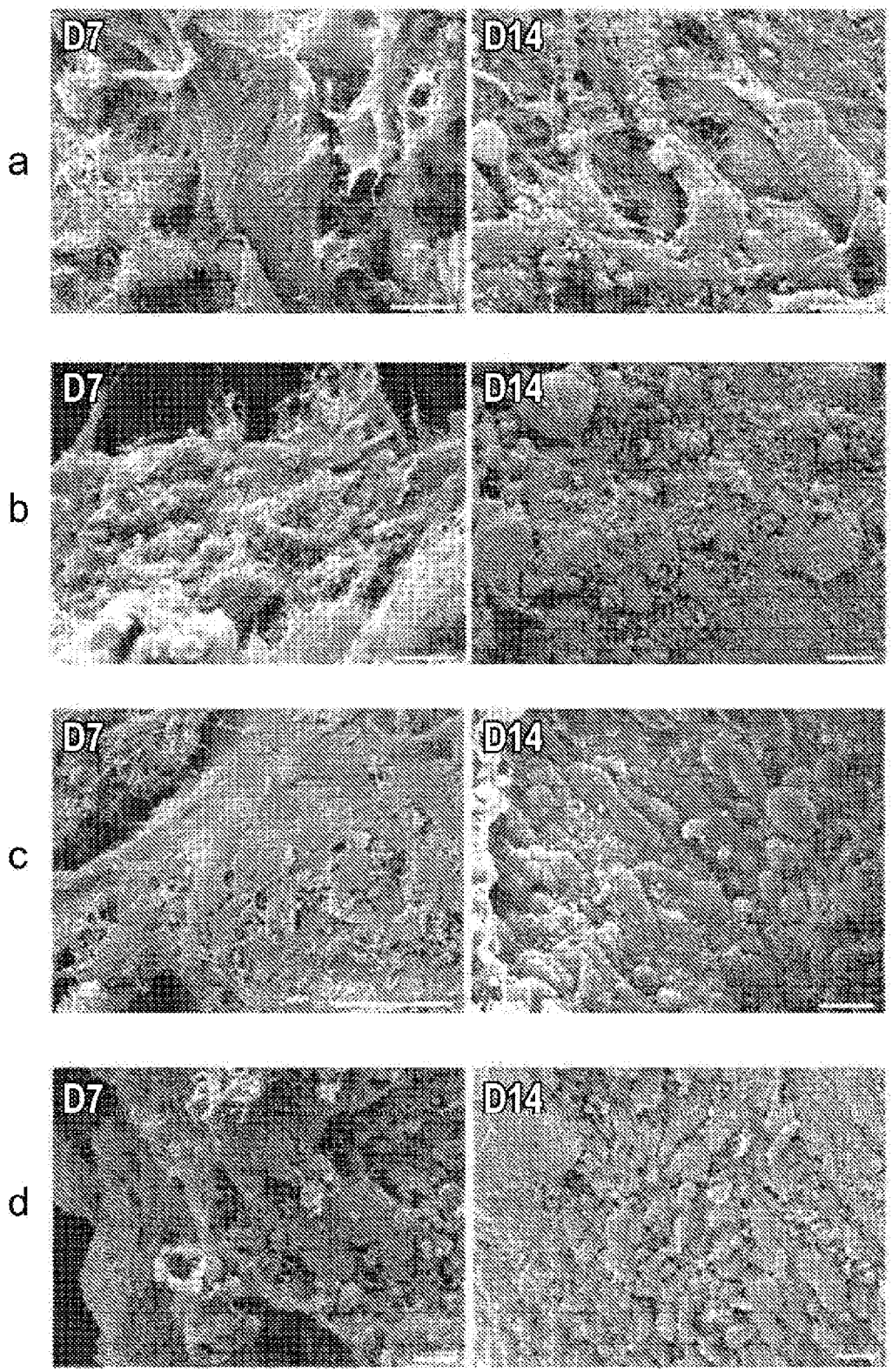
FIG. 21 illustrates the calcium deposition and cell morphology of the CAF gels after incubation for 7 and 14 days in osteogenic medium.

FIG. 21 shows calcium deposition and cell morphology after incubation during 7 and 14 days in osteogenic medium by scanning electron microscopy. FIGS. 21a and 21b show the calcium deposition on low and high cell density hydrogels, respectively. A faster and increased deposition is possible to be verified on $40 \times 10^6$ cells/mL hydrogels. FIGS. 21c and 21d demonstrate how MSC morphology change during differentiation for low and high cell density samples, respectively. Cuboidal cells are already observable by day 7 on $40 \times 10^6$ cells/mL hydrogels. The same only happens after 14 days of differentiation on low cell density specimens. Scale bars represent 10 µm (a and b) and 20 µm (c and d). Accordingly, FIG. 21 illustrates greater calcium deposition and earlier emergence of cuboidal osteoblast cells with the higher cell density.

Figure 22:
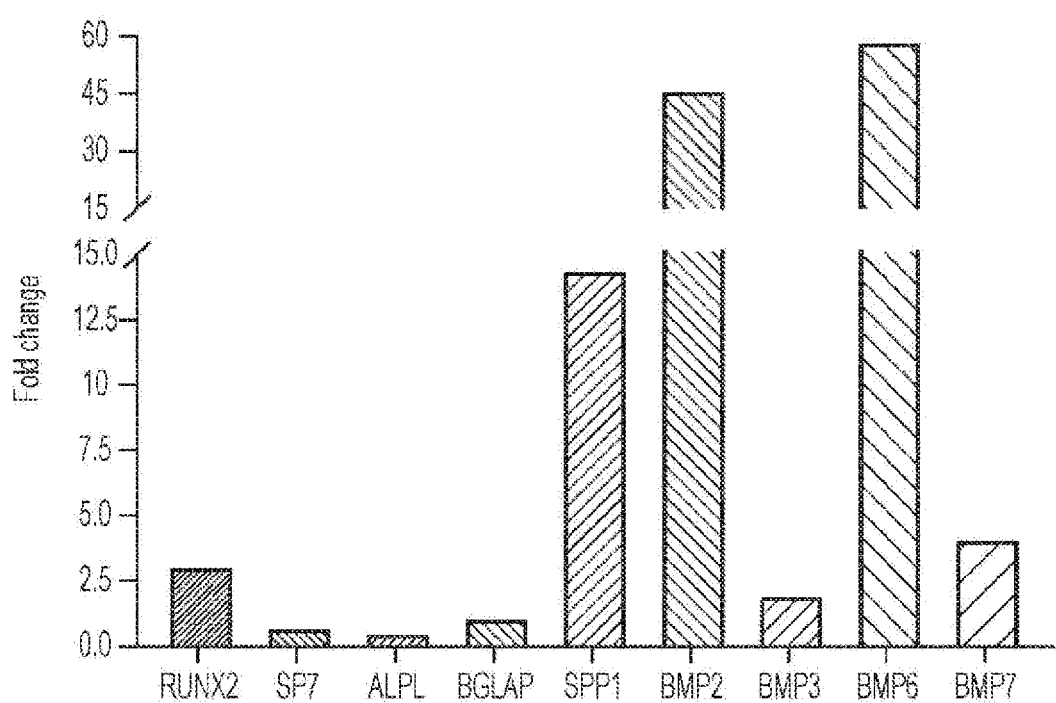
FIG. 22 illustrates osteogenic gene and protein expression between the two gels by comparison of fold change between the gels after incubation for 14 days in osteogenic medium.

FIG. 22 shows osteogenic gene and protein expression in terms of fold change of selected osteogenic gene and protein markers, comparing the 40 million cells per mL gel at day 14 to the 4 million cells per mL gel at day 14, respectively. At day 14, $40 \times 10^6$ cells/mL loaded gels present gene expression that reflects mature osteoblast formation, contrarily to $4 \times 10^6$ cells/mL loaded gels that show pre-to-early osteoblast related gene expression. Hence, this PCR array data, comparing the expression of bone genomic and proteomic markers within both tissues, shows that the high cell density micro-tissue has much higher expression of osteopontin (SPP1) and bone morporphogenic proteins 2 and 6 (BMP-2 and BMP-6). This indicates that the micro-tissue produced with the higher cell density is more mature. Taken overall these results indicate, using bone as a model system, that the high cell density achievable with the printing apparatus of the invention has a clear impact on the speed with which mature micro-tissues can be made.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the present invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The present invention is not restricted to the details of any foregoing embodiments. The present invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A 3D bioprinting apparatus for impinging liquids from at least two liquid sources,
the apparatus comprising:
a first jet actuator configured to dispense a first liquid from a first liquid source;
a second jet actuator configured to dispense a second liquid from a second liquid source; and
an adjustment element comprising an actuating element, a biasing element and a controller,
wherein the actuating element is configured to adjust the position of the first jet actuator relative to the second jet actuator to adjust a trajectory of the first liquid dispensed from the first jet actuator such that the first liquid impinges the second liquid dispensed from the second jet actuator;
wherein the biasing element is arranged to oppose a force of the actuating element on the first jet actuator; and
wherein the controller is configured to time the release of at least the first liquid dispensed from the first jet actuator such that the first liquid impinges and combines mid-air with the second liquid dispensed from the second jet actuator.

2. The 3D bioprinting apparatus according to claim 1, wherein the adjustment element is configured to effect translational movement of the first jet actuator with respect to the second jet actuator.

3. The 3D bioprinting apparatus according to claim 1, wherein the adjustment element is configured to effect rotational movement of the first jet actuator.

4. The 3D bioprinting apparatus according to claim 1, wherein the controller controls the actuating element.

5. The 3D bioprinting apparatus according to claim 1, wherein the adjustment element further comprises a further biasing element arranged to apply a force to the first jet actuator to control rotational movement of the first jet actuator upon actuation of the actuating element.

6. The 3D bioprinting apparatus according to claim 1, wherein the adjustment element is configured to apply a force to the first liquid after it is dispensed from the first jet actuator to adjust the trajectory of the first liquid.

7. The 3D bioprinting apparatus according to claim 6, wherein the adjustment element comprises electrically charged deflection plates for applying an electrostatic force to the first liquid.

8. The 3D bioprinting apparatus according to claim 7, wherein the charged deflection plates are positioned adjacent to an exit nozzle of the first jet actuator.

9. The 3D bioprinting apparatus according to claim 1, wherein the first and second jet actuators are configured as drop-on-demand actuators.

10. The 3D bioprinting apparatus according to claim 1, further comprising a jet controller for controlling the release of the first and second liquids from the respective first and second jet actuators.

11. The 3D bioprinting apparatus according to claim 1, wherein one or both of the first liquid and the second liquid comprises viable cells.

12. A method of use of the 3D bioprinting apparatus according to claim 1, for producing a gel comprising viable cells, wherein the first liquid source or the second liquid source has a concentration of 10 million to 90 million cells per ml.

13. A method of 3D printing comprising:
providing a first jet actuator configured to dispense a first liquid from a first liquid source;
providing a second jet actuator configured to dispense a second liquid from a second liquid source;
adjusting, with an adjustment element comprising an actuating element, a biasing element and a controller, a trajectory of at least the first liquid dispensed from the first jet actuator such that the first liquid impinges and combines mid-air with the second liquid dispensed from the second jet actuator; wherein the biasing element is arranged to oppose a force of the actuating element on the first jet actuator;
and depositing the combined first and second liquid on a substrate.

14. The method according to claim 13, wherein the first liquid comprises a first gel precursor and the second liquid comprises a second gel precursor.

15. The method according to claim 14, wherein at least one of the first and second gel precursors comprise biological materials.

16. The method according to claim 15, wherein the first liquid comprises a first reactive polymer precursor and the second liquid comprises a second reactive polymer precursor.

17. A method of preparing a gel comprising viable cells, said method comprising 3D printing the gel using the 3D bioprinting apparatus of claim 1, wherein either the first or second jet actuator is configured to dispense a liquid comprising viable cells and the first and second liquid combine to form a gel.

18. A method of preparing a gel comprising viable cells, said method comprising the method steps of claim 13, wherein either the first and/or second liquid comprises viable cells and the liquids combine to form a gel.

19. The method according to claim 17, wherein the gel comprises cells at a concentration of between 10 million and 90 million cells per ml.

* * * * *